(12) United States Patent
Dorris et al.

(10) Patent No.: US 7,552,013 B2
(45) Date of Patent: Jun. 23, 2009

(54) RATIO-BASED OLIGONUCLEOTIDE PROBE SELECTION

(75) Inventors: David Dorris, Glenview, IL (US); Abhijit Mazumder, Buffalo Grove, IL (US); Richard D. Shippy, Scottsdale, AZ (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 454 days.

(21) Appl. No.: 11/375,981

(22) Filed: Mar. 15, 2006

(65) Prior Publication Data

US 2006/0155484 A1  Jul. 13, 2006

Related U.S. Application Data

(62) Division of application No. 09/921,045, filed on Aug. 2, 2001, now Pat. No. 7,047,141.

(60) Provisional application No. 60/278,074, filed on Mar. 22, 2001.

(51) Int. Cl.
*G06F 19/00* (2006.01)
*C12Q 1/68* (2006.01)

(52) U.S. Cl. ............................. 702/19; 435/6

(58) Field of Classification Search ........................ None
See application file for complete search history.

(56) References Cited

U.S. PATENT DOCUMENTS

| | | | |
|---|---|---|---|
| 5,474,796 A | 12/1995 | Brennan | |
| 5,968,740 A | 10/1999 | Fodor et al. | |
| 5,985,551 A | 11/1999 | Brennan | |
| 6,001,311 A | 12/1999 | Brennan | |
| 6,040,138 A * | 3/2000 | Lockhart et al. | ............ 435/6 |
| 6,210,894 B1 | 4/2001 | Brennan | |
| 6,228,575 B1 | 5/2001 | Gingeras et al. | |
| 6,268,152 B1 | 7/2001 | Fodor et al. | |
| 6,284,460 B1 | 9/2001 | Fodor et al. | |
| 6,344,316 B1 | 2/2002 | Lockhart et al. | |

FOREIGN PATENT DOCUMENTS

| | | |
|---|---|---|
| WO | WO 99/13105 | 3/1999 |
| WO | WO 01/05935 | 1/2001 |
| WO | WO 01/06013 | 1/2001 |

OTHER PUBLICATIONS

Alizadeh, A., et al., "Distinct Types of Diffuse Large B-cell Lymphoma Identified by Gene Expression Profiling", *Nature*, vol. 403, 2000, p. 503-511.
Beiβbarth, T., et al., "Processing and Quality Control of DNA Array Hybridization Data", *Bioinformatics*, vol. 16, No. 11, 2000, p. 1014-1022.
Duggan, D., et al., "Expression Profiling Using cDNA Microarrays", *Nature Genetics Supplement*, vol. 21, 1999, p. 10-14.
Li, F., et al., "Selection of Optimal DNA Oligos for Gene Expression Arrays", *Bioinformatics*, vol. 17, No. 11, 2001, p. 1067-1076.
Lipshutz, R., et al., "High Density Synthetic Oligonucleotide Arrays", *Nature Genetics Supplement*, vol. 21, 1999, p. 20-24.
Lockhart, D., et al., "Expression Monitoring by Hybridization to High-Density Oligonucleotide Arrays", *Biotechnology*, vol. 14, No. 3, 1996, p. 1675-1680.
Manduchi, E., et al., "Generation of Patterns from Gene Expression Data by Assigning Confidence to Differentially Expressed Genes", *Bioinformatics*, vol. 16, No. 8, 2000, p. 685-698.
Ramakrishnan, R., et al., "An Assessment of Motorola CodeLink™ Microarray Performance for Gene Expression Profiling Applications", *Nucleic Acids Research*, vol. 30, No. 7, 2002, p. 1-12.
Tomiuk, S., et al., "Microarray Probe Selection Strategies", *Briefings in Bioinformatics*, vol. 2, No. 4, 2001, p. 329-340.
Yue, H., et al., "An Evaluation of the Performance of cDNA Microarrays for Detecting Changes in Global mRNA Expression", *Nucleic Acids Research*, vol. 29, No. 8, 2001, p. E41-1-E41-9.

* cited by examiner

*Primary Examiner*—John S Brusca
(74) *Attorney, Agent, or Firm*—Yonggang Ji

(57) ABSTRACT

Disclosed herein are methods of selecting probes to target nucleic acid sequences, methods of making oligonucleotide arrays comprising such probes, and methods of using such arrays. Also, described herein are oligonucleotide arrays comprising probes selected by a method of the invention.

2 Claims, No Drawings

RATIO-BASED OLIGONUCLEOTIDE PROBE SELECTION

CROSS REFERENCE TO RELATED APPLICATIONS

This application is a divisional of U.S. patent application Ser. No. 09/921,045 filed Aug. 2, 2001, now U.S. Pat. No. 7,047,141 which claims priority to U.S. provisional patent application No. 60/278,074 filed Mar. 22, 2001, the disclosures of which are incorporated herein by reference in their entireties.

BACKGROUND OF THE INVENTION

Oligonucleotide arrays contain probes of known nucleic acid sequence on specific regions of a substrate, each region containing probes of a different nucleic acid sequence. A composition comprising target nucleic acid molecules (e.g., mRNA or cDNA from a cell) is allowed to hybridize with the probes of the array under conditions favoring hybridization of probes and target nucleic acid molecules complementing without mismatches. Unhybridized target nucleic acids are washed away and hybridization is detected.

The target molecule typically is labeled with a detectable molecule, such as a fluorophore. The presence of the target nucleic acid (and therefore hybridization) may be determined by the detection of the detectable molecule. Because the nucleic acid sequence of the probe in each region of the array is known, detection of hybridization within a region indicates that the composition contained a target nucleic acid having the complement to the probe. Furthermore, in certain situations, the level of detection correlates with the concentration of the target nucleic acid.

Gene expression profiling is a powerful tool for target discovery, gene function elucidation, drug target identification, and toxicity profiling. Oligonucleotide arrays enable one to query each of these issues with high specificity and in an expeditious manner, obviating the need for clone tracking and handling and the need for upfront PCR preparation and purification. To accurately perform gene expression profiling with an oligonucleotide array, one or more probes complementary to the gene are present in the array.

Because the probes typically are of such length that they cannot contain the entire nucleic acid sequence of the gene, probes must be chosen that are complementary to only a portion of the gene. It is preferable that the probes chosen are able to accurately indicate the expression level of the gene. Due to the differences of oligonucleotide sequences and the ramifications on hybridization kinetics and thermodynamics, all probes do not give equivalent hybridization signals even when the target nucleic acid concentrations are equal. Often multiple probes to a single gene are contained within the array to provide for greater specificity and accuracy.

However, with post-synthetic covalent attachment schemes, it is important to arrive at a limited number of probes to be dispensed per gene in order to keep costs down and gene density up, allowing more genes to be analyzed on a single array. The mechanism by which most companies arrive at this limited number of probes is by a process called rapid prototyping, in which a superset of probes is generated and hybridized to the intended target and the one which gives the highest hybridization signal is chosen. Lockhart et al., in U.S. Pat. No. 6,040,138, describe such a method. In that patent, a number of candidate probes to a target sequence are tested to determine which probe provided the strongest signal. In an attempt to account for probes that show a high background signal even in the absence of the target, Lockhart et al. compare the probe signal to a signal obtained from a second probe constructed to contain a single mismatch with the target sequence. Only those probes having a signal that is a certain percentage over the signal obtained with the mismatch probe are used. Lockhart et al. describe using multiple probes for a given target sequence in an array to accurately determine the expression level of a gene over a range of concentrations.

Ideally, an array would contain only one probe for each gene yet still would be able to provide accurate differential gene expression profiles. Because a probe giving the highest hybridization signal at a given concentration of intended target (chosen by rapid prototyping) may not always provide for accurate gene expression profiles wherein different samples have varying amounts or varying structures of the intended target, there is a need for arrays containing only a single probe to each gene yet are still able to indicate variation in the expression level of the gene.

BRIEF SUMMARY OF THE INVENTION

In a preferred embodiment, the present invention includes an oligonucleotide array containing only a single probe for each gene, yet capable of accurately indicating the relative expression level of each gene. Rather than a rapid prototyping method wherein the probe that provides the highest signal is chosen, the present invention includes a novel method of choosing probes referred to herein as ratio-based prototyping.

In ratio-based prototyping, whether the probe provides a high or low hybridization signal is not determinative. Rather, a ratio of hybridization signals obtained from contacting a candidate probe with different concentrations of a target sequence is calculated. A hybridization signal ratio is calculated for two or more additional candidate probes to a target sequence. In certain embodiments, an average of all of the hybridization signal ratios is then determined and the probe is selected by comparing a probe's hybridization signal ratio to the average of the hybridization signal ratios. Preferably, the probe having a hybridization signal ratio closest to the average of the hybridization signal ratios is selected. In other embodiments, a concentration ratio is calculated and the probe is selected by comparing a probe's hybridization signal ratio to the concentration ratio. Preferably, the probe having a hybridization signal ratio closest to the concentration ratio is selected.

Definitions

The terms "nucleic acid" or "nucleic acid molecule" refer to a deoxyribonucleotide or ribonucleotide polymer in either single- or double-stranded form. Such nucleic acids, unless otherwise limited, would encompass known analogs of natural nucleotides that can function in a similar manner as naturally occurring nucleotides (e.g., protein nucleic acids).

The term "oligonucleotide" refers to is a single-stranded nucleic acid ranging in length from 2 to about 500 bases.

The term "probe" refers to an oligonucleotide capable of binding to a target nucleic acid of complementary sequence through one or more types of chemical bonds, usually through complementary base pairing, Watson-Crick base pairing. As used herein, an oligonucleotide probe may include natural (ie. A, G, C, or T) or modified bases (7-deazaguanosine, inosine, etc.). In addition, the bases in oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages.

The term "target nucleic acid sequence" refers to a nucleic acid (often derived from a biological sample), to which the oligonucleotide probe is designed to specifically hybridize. The target nucleic acid has a sequence that is complementary to the nucleic acid sequence of the candidate probe directed to the target. The term target nucleic acid may refer to the specific subsequence of a larger nucleic acid (e.g., an alternatively spliced exon) to which the probe is directed or to the overall sequence (e.g., gene or mRNA) whose expression level it is desired to detect. The difference in usage will be apparent from context.

The term "candidate probe" refers to any oligonucleotide probe that is complementary to a particular target nucleic acid sequence. The candidate probes will differ between different target sequences.

As used herein, the term "hybridizing" refers to the process of incubating the candidate probes with a composition comprising nucleic acids under stringent conditions. The term "stringent conditions" refers to conditions under which a probe will hybridize to its target subsequence, but weakly or not at all to other sequences. The term "hybridize" means two nucleic acids form complementary base pairing between each other. Stringent conditions are sequence- and length-dependent and may be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the probe sequences are generally present in excess, at Tm, 50% of the targets are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

As used herein, "expressed sequence" refers to a nucleic acid sequence that is transcribed within a cell, such as an mRNA or ribosomal RNA.

As used herein, "binding pair" refers to two molecules that are capable of physically interacting with high affinity. Examples of binding pairs include, but are not limited to, antibody-antigen, avidin (streptavidin)-biotin, and receptor-ligand. For matter of clarity, binding pair does not refer to the probe and the target nucleic acid sequence.

DETAILED DESCRIPTION OF THE INVENTION

This invention provides methods of choosing probes to a target sequence (e.g., a gene), particularly probes for use in high-density oligonucleotide arrays. Because the present method provides for probes that allow for the accurate determination of the amount of target sequence within a composition over a wide range of concentrations, the use of multiple probes per gene may be obviated. Thus, such probes are useful in methods of accurately analyzing the expression of a gene within a cell or group of cells using only a single probe. The present invention also provides oligonucleotide arrays comprising such probes that are useful for accurately analyzing, at the same time, the expression of many genes within a cell or group of cells using only one probe per gene.

The present invention provides a method of selecting a probe for a target nucleic acid sequence. In one embodiment, three or more candidate probes are hybridized with a first composition comprising the target nucleic acid. A first hybridization signal is then determined for each of the candidate probes. (The determination of the hybridization signal may be repeated several times for each candidate probe and an average of all the determinations may be used in subsequent steps of the method). The candidate probes are then hybridized with a second composition comprising the target nucleic acid and a second hybridization signal is determined. A hybridization signal ratio is then calculated for each candidate probe. This ratio is the ratio of the first hybridization signal to the second hybridization signal for each candidate probe. These hybridization signal ratios from all the candidate probes are then averaged. The hybridization signal ratio from each candidate probe is then compared to the average hybridization signal ratio in order to chose which of the candidate probes is the appropriate probe for that target sequence. In a preferred embodiment, the candidate probe having a hybridization signal ratio closest to the average hybridization signal ratio is chosen.

In an alternative embodiment, the above method further comprises hybridizing the candidate probes with a third composition comprising the target nucleic acid, determining a third hybridization signal for each candidate probe, calculating a second hybridization signal ratio (the first hybridization signal to the third hybridization signal) or a third hybridization signal ratio (the second hybridization signal to the third hybridization signal) for each candidate probe, calculating an average second hybridization signal ratio for the three or more candidate probes (or an average third hybridization signal ratio for the three or more candidate probes), and selecting the appropriate probe by comparing a candidate probe's second hybridization signal ratio to the average second hybridization signal ratio (or by comparing a candidate probe's third hybridization signal ratio to the average third hybridization signal ratio). In a preferred embodiment, the candidate probe having a second hybridization signal ratio closest to the average second hybridization signal ratio is chosen (or the candidate probe having a third hybridization signal ratio closest to the average third hybridization signal ratio).

In a more preferred embodiment, the appropriate candidate probe is chosen by comparing the candidate probe's hybridization signal ratio and a second hybridization signal ratio to the average hybridization signal ratio and average second hybridization signal ratio. In an even more preferred embodiment, the candidate probe having a hybridization signal ratio and second hybridization signal ratio closest to the average hybridization signal ratio and average second hybridization signal ratio is chosen. In yet more preferred embodiment, the candidate probe having a hybridization signal ratio, second hybridization signal ratio, and third hybridization signal ratio closest to the average hybridization signal ratio, average second hybridization signal ratio, and average third hybridization signal ratio, respectively, is chosen.

This process may be continued using a fourth composition, fifth composition, sixth composition, etc. to obtain additional hybridization signal ratios and average signal ratios.

In another embodiment, the relative concentration of the target nucleic acid within the first composition and the second composition is known. This allows a calculation of a concentration ratio (relative concentration of target nucleic acid in first composition to relative concentration of target nucleic acid in second composition). To chose the appropriate probe, this concentration ratio is then compared to the candidate probe's hybridization signal ratio calculated by hybridizing the candidate probes with the first composition to determine a first hybridization signal, hybridizing the candidate probes with the second composition to determine a second hybridization signal, and calculating the ratio of the first hybridization signal to the second hybridization signal. In a preferred embodiment, the probe having a hybridization signal ratio closest to the concentration ratio is chosen.

The target nucleic acid may be essentially any nucleic acid sequence. It may be RNA or DNA, double stranded or single stranded. The target nucleic may be an unexpressed region of a genome, such as a promoter or an enhancer. Alternatively, the target nucleic acid may be an expressed sequence, such as a gene or ribosomal RNA. The target nucleic acid may be of essentially any origin including prokaryotic, eukaryotic, archea, and viral. In preferred embodiments, the eukaryote is a mammal, more preferably rat, even more preferably human. When a target nucleic acid is said to "derive" from a source, it is meant that the target nucleic acid is isolated from a particular source. Thus, an RNA derived from a human cell is RNA isolated from a human cell. Of course, further processing steps may be included, e.g., conversion of RNA to cDNA. Thus, a target nucleic acid derived from a human cell may be a cDNA produced from isolating PolyA$^+$ RNA from a human cell.

Because the target nucleic acid is typically longer than the desired length of a probe to that sequence, e.g., 30 nt, there are a large number of candidate probes to any given target nucleic acid. To help narrow down the number of candidate probes to be tested, the probes may first be validated by quantitative PCR or quantitative nuclease protection assay. The sequence of the candidate probes may be used in a search in a nucleic acid database, such as the human genome database or a database of expressed sequences, to screen those probes having redundancy with other sequences. Furthermore, particularly in methods wherein detection of an cDNA derived from an mRNA is desired, it is preferable that the candidate probes be complementary to the 3' end of the cDNA rather than the 5' end. This is because cDNA production methods often result in cDNAs wherein the 5' end is truncated at compared to the mRNA from which it was derived.

Essentially any number of candidate probes, limited only by the length of the target sequence, may be used in the methods of the present invention. Preferably at least three candidate probes are used. More preferably, at least 4, at least 5, at least 6, at least 7, at least 8, at least 9, at least 10, or more probes are used. In preferred embodiments, the candidate probes are of differing sequence and complementary to the target sequence without mismatch.

The candidate probes may range from about 5 to about 500 nucleotides, more preferably from about 10, about 15, about 20, or about 25, to about 30, about 35, about 40, about 50, or about 100 nucleotides in length. The candidate probes may be within an oligonucleotide array.

Compositions comprising the target nucleic acid may be produced from a number of sources. For example, the composition may be derived from a particular tissue or cell type. Alternatively, the composition may be derived from a cell grown under specified growth conditions. Furthermore, the composition may be produced by diluting a stock comprising the target sequence. In preferred embodiments, the first, second, or subsequent compositions used in the methods of the present invention contain different concentrations of the target sequence. For example, the first composition is derived from mRNA from one tissue type and the second composition is derived from mRNA from a different tissue type; or the first composition is derived from mRNA from a cell grown at one culture condition and the second composition is derived from mRNA from a cell grown at a second culture condition. One of skill in the art would understand that there any many ways in which one could produce the various compositions comprising the target nucleic acid for use in the methods of the present invention.

The compositions comprising the target nucleic acid are hybridized to the candidate probes. It is preferable that the hybridization be under stringent conditions such that sequences comprising one or more mismatches to a candidate probe are washed away. As discussed below, there are many methods known in the art to produce stringent hybridization conditions. Furthermore, methods are known in which the composition comprising the target nucleic acid may be modified to increase the signal to noise ratio.

After hybridization, and subsequent washes, it is necessary to produce a hybridization signal from the target nucleic acid hybridized to the candidate probes. Typically, this is accomplished by labeling the target nucleic acid with a detectable marker or label. The target nucleic acid may be labeled prior to hybridization or hybridization may take place and then the target nucleic acid is labeled. For example, the target nucleic acid may be biotinylated and, after hybridization, contacted with avidin or spteptavidin linked to a label, e.g., fluorescein. Methods in which the target nucleic acids may be labeled, different labels that may be used, and methods of detecting the labels are well known in the art and discussed below.

Oligonucleotide Arrays

The probes selected by the methods of the present invention may be incorporated into an oligonucleotide array. In preferred embodiments, the oligonucleotide arrays of the present invention comprise only one probe per target sequence (e.g., gene or alternative splicing product) and at least 80%, at least 85%, at least 90%, at least 95%, at least 99% or 100% of the probes of the array are targeted to a different target sequence. Furthermore, the arrays of the present invention may comprise at least 10, at least 100, at least 1000, at least 5000, at least 10000, or at least 50000 probes selected by a method of the present invention. In some embodiments, the array contains probes to a single species. The species may be any species including archea species, prokaryotic species, eukaryotic species, or viral species. Preferred eukaryotic species include mammalian species, such as rat or human.

Methods of forming high density arrays of oligonucleotides, peptides and other polymer sequences with a minimal number of synthetic steps are known. In preferred embodiments, the oligonucleotides of the array are attached to a hydrogel. Methods of making hydrogel arrays are well-known in the art. A preferred method of attaching an oligonucleotide probe to a hydrogel array is by 2+2 photocycloaddition (disclosed in WO 01/01143, which is incorporated herein by reference in its entirety). In a more preferred embodiment, the oligonucleotides are attached to NHS-esters of thin films (Yan et al., *Bioconjug Chem* 1994 March-April; 5(2):151-7).

Alternatively, the oligonucleotide array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays of peptides, oligonucleotides and other molecules using, for example, light-directed synthesis techniques. See also, Fodor et al., Science, 251, 767-77 (1991). These procedures for synthesis of polymer arrays are now referred to as VLSIPS™ (very large scale immobilized polymer synthesis) procedures. Using the VLSIPS™ approach, one heterogenous array of polymers is converted, through simultaneous coupling at a number of reaction sites, into a different heterogenous array. See, U.S. application Ser. Nos. 07/796,243 and 07/980,523.

In brief, the light-directed combinatorial synthesis of oligonucleotide arrays on a glass surface proceeds using automated phosphoramidite chemistry and chip masking techniques. In one specific implementation, a glass surface is derivatized with a saline reagent containing a functional group, e.g., a hydroxyl or amine group blocked by a photolabile protecting group. Photolysis through a photolithogaphic mask is used selectively to expose functional groups that are then ready to react with incoming 5'-photoprotected nucleoside phosphoramidites. The phosphoramidites react only with those sites that are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., U.S. Pat. No. 5,143,854.

Peptide (protein) nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotides" for purposes of this disclosure.

In addition to the foregoing, additional methods that can be used to generate an array of oligonucleotides on a single substrate are known in the art, e.g., PCT Publication No. WO 93/09668. Such methods include applications in which reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In some embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

Hybridization

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37° C. (0.005% Triton X-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g., down to as low as 0.25×SSPE-T at 37° C. to 50° C.) until a desired level of hybridization specificity is obtained. Stringency can also be increased by addition of agents such as formamide. Hybridization specificity may be evaluated by comparison of hybridization to test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In some embodiments, background signal is reduced by the use of a detergent (e.g., CTAB) or a blocking reagent (e.g., sperm DNA, cot-1 DNA, etc.) during the hybridization to reduce non-specific binding. In a preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.).

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability (Tm) of the duplex formed between the target and the probe using, e.g., known oligonucleotides allows for optimization of duplex stability and mismatch discrimination. One useful aspect of altering the Tm arises from the fact that adenine-thymine (A-T) duplexes have a lower Tm than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it may not be possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide probes can be ascertained by following, e.g., fluorescence signal intensity of oligonucleotide arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous studies using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1993)).

Signal Detection

Means of detecting labeled target (sample) nucleic acids hybridized to the probes of the oligonucleotide array are known to those of skill in the art. Thus, for example, where a calorimetric label is used, simple visualization of the label is sufficient. Where a radioactive labeled probe is used, detection of the radiation (e.g with photographic film or a solid state detector) is sufficient.

In a preferred embodiment, however, the target nucleic acids are labeled with a fluorescent label and the localization of the label on the probe array is accomplished with a microscope. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire array. Similarly, the microscope may be equipped with a phototransducer (e.g., a photomultiplier, a solid state array, a ccd camera, etc.) attached to an automated data acquisition system to automatically record the fluorescence signal produced by hybridization to each oligonucleotide probe on the array. Such automated systems are described at length in U.S. Pat. No. 5,143,854 and PCT application WO 92/10092.

Signal Evaluation

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In some embodiments, a suitable threshold is about 10% above that of the average background signal. In addition, the provision of appropriate controls permits a more detailed analysis that controls for variations in hybridization conditions, cell health, non-specific binding and the like. Thus, for example, in a preferred embodiment, the hybridization array is provided with normalization controls. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average or median signal produced by the normalization controls. Normalization may also include correction for variations due to sample preparation and amplification. Such normalization may be accomplished by dividing the measured signal by the average signal from the sample preparation/amplification control probes (e.g., the Bio B probes). The resulting values may be multiplied by a constant value to scale the results.

Preferred high density arrays of this invention comprise greater than about 100, preferably greater than about 1000, more preferably greater than about 5,000 and most preferably greater than about 10,000 or even greater than about 50,000 different oligonucleotide probes. The oligonucleotide probes range from about 5 to about 100 nucleotides, more preferably from about 10, or about 15, or about 20, or about 25, to about 30, or about 35, or about 40, or about 50 nucleotides in length.

The location and sequence of each different oligonucleotide probe sequence in the array is known. Moreover, the large number of different probes occupy a relatively small area providing a high density array having a probe density of generally greater than about 60, more generally greater than about 100, most generally greater than about 600, often greater than about 1000, more often greater than about 5,000, most often greater than about 10,000, preferably greater than about 40,000 or more preferably greater than about 100,000, and most preferably greater than about 400,000 different oligonucleotide probes per $cm^2$. The small surface area of the array (often less than about 10 $cm^2$, preferably less than about 5 $cm^2$, more preferably less than about 2 $cm^2$, and most preferably less than about 1.6 $cm^2$) permits extremely uniform hybridization conditions (temperature regulation, salt content, etc.).

Controls may be included in the oligonucleotide arrays of the present invention. For example, controls that may be included include probes for variations or mutations in a particular gene, controls for overall hybridization conditions, controls for sample preparation conditions, controls for metabolic activity of the cell from which the nucleic acids are derived and mismatch controls for non-specific binding or cross hybridization. Controls may include probes corresponding to bacterial nucleic acid sequences or biotinylated generic nucleic acid sequences.

Methods of Monitoring Gene Expression

The oligonucleotide arrays of the present invention are particularly useful in methods of monitoring gene expression. Because the probes selected by the methods of the present invention provide for accurate assessment of a wide range of gene expression using only a single probe per gene, the expression of a large number of genes may be determined simultaneously. The only limitation to the number of genes that can be monitored simultaneously is the number of probes that can be placed on a single array and accurately read. Thus, using an array of the present invention at least 10, at least 100, at least 1,000, at least 5,000, at least 10,000, at least 15,000, at least 20,000, at least 25,000, at least 30,000, at least 40,000, or at least 50,000 genes may be monitored simultaneously.

Methods of monitoring gene expression using oligonucleotide arrays are well known in the art. Lockhart et al. in U.S. Pat. No. 6,040,138, incorporated herein by reference in its entirety, describe the use of oligonucleotide arrays to analyze the expression of a multiplicity of genes and the construction of such arrays. One of skill in the art would understand that the probes chosen by a method of the present invention may easily be substituted for the probes described in Lockhart et al., or any other oligonucleotide array, and used in gene expression analysis as described therein.

Generally the methods of monitoring gene expression of this invention involve (1) providing a pool of target nucleic acids comprising RNA transcript(s) of one or more target gene(s), or nucleic acids derived from the RNA transcript(s); (2) hybridizing the nucleic acid sample to a high density array of probes (including control probes); and (3) detecting the hybridized nucleic acids and calculating a relative expression (transcription) level.

Providing a Nucleic Acid Sample.

One of skill in the art will appreciate that in order to measure the transcription level (and thereby the expression level) of a gene or genes, it is desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

In a particularly preferred embodiment, where it is desired to quantify the transcription level (and thereby expression) of a one or more genes in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired, no elaborate control or calibration is required.

In the simplest embodiment, such a nucleic acid sample is mRNA isolated from a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Methods of isolating total mRNA are well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993).

In one embodiment, the total nucleic acid is isolated from a given sample using, for example, an acid guanidinium-phenol-chloroform extraction method and polyA$^+$ mRNA is isolated by oligo dT column chromatography or by using (dT)n magnetic beads (see, e.g., Sambrook et al., Molecular Cloning: A Laboratory Manual (2nd ed.), Vols. 1-3, Cold Spring Harbor Laboratory, (1989), or Current Protocols in Molecular Biology, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The oligonucleotide array may then include probes specific to the internal standard for quantification of the amplified nucleic acid.

One internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al., Academic Press, Inc. N.Y., (1990).

Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

In another embodiment, the sample mRNA is reverse transcribed with a reverse transcriptase and a primer consisting of oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., Proc. Natl. Acad. Sci. USA, 87: 1663-1667 (1990) who demonstrate that in vitro amplification according to this method preserves the relative frequencies of the various RNA transcripts. Moreover, Eberwine et al. Proc. Natl. Acad. Sci. USA, 89: 3010-3014 provide a protocol that uses two rounds of amplification via in vitro transcription to achieve greater than $10^6$ fold amplification of the original starting material thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lamda vectors designed for Cre-loxP plasmid subcloning (see e.g., Palazzolo et al., Gene, 88: 25-36 (1990)).

Labeling Nucleic Acids.

In a preferred embodiment, the hybridized nucleic acids are detected by detecting one or more labels attached to the sample nucleic acids. The labels may be incorporated by any of a number of means well known to those of skill in the art. For example, the label may be simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore). Alternatively, the nucleic acids may be biotinylated and subsequently contacted with a label linked to avidin or streptavidin.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization With Nucleic Acid Probes, P. Tijssen, ed. Elsevier, N.Y., (1993)).

Fluorescent labels are preferred and easily added during an in vitro transcription reaction. In one embodiment, fluorescein labeled UTP and CTP are incorporated into the RNA produced in an in vitro transcription reaction as described above. In another embodiment, the nucleic acids are biotinylated. Such biotinylated nucleic acids may be detected using labeled streptavidin.

Modifying a Sample to Improve Signal/Noise Ratio.

The nucleic acid sample may be modified prior to hybridization to the oligonucleotide array in order to reduce sample complexity thereby decreasing background signal and improving sensitivity of the measurement. In one embodiment, complexity reduction is achieved by selective degradation of background mRNA. This is accomplished by hybridizing the sample mRNA (e.g., polyA.$^+$RNA) with a pool of DNA oligonucleotides that hybridize specifically with the regions to which the probes in the array specifically hybridize. In a preferred embodiment, the pool of oligonucleotides consists of the same probe oligonucleotides as found on the high density array.

The pool of oligonucleotides hybridizes to the sample mRNA forming a number of double stranded (hybrid duplex) nucleic acids. The hybridized sample is then treated with RNase A, a nuclease that specifically digests single stranded RNA. The RNase A is then inhibited, using a protease and/or commercially available RNase inhibitors, and the double stranded nucleic acids are then separated from the digested single stranded RNA. This separation may be accomplished in a number of ways well known to those of skill in the art including, but not limited to, electrophoresis, and gradient centrifugation. However, in a preferred embodiment, the pool of DNA oligonucleotides is provided attached to beads forming thereby a nucleic acid affinity column. After digestion with the RNase A, the hybridized DNA is removed simply by denaturing (e.g., by adding heat or increasing salt) the hybrid duplexes and washing the previously hybridized mRNA off in an elution buffer.

The undigested mRNA fragments which will be hybridized to the probes in the high density array may then be end-labeled with a fluorophore attached to an RNA linker using an RNA ligase. This procedure produces a labeled sample RNA pool in which the nucleic acids that do not correspond to probes in the array are eliminated and thus unavailable to contribute to a background signal.

Another method of reducing sample complexity involves hybridizing the mRNA with deoxyoligonucleotides that hybridize to regions that border on either side the regions to which the high density array probes are directed. Treatment with RNAse H selectively digests the double stranded (hybrid duplexes) leaving a pool of single-stranded mRNA corresponding to the short regions (e.g., 20 mer) that were formerly bounded by the deoxyolignucleotide probes and which correspond to the targets of the high density array probes and longer mRNA sequences that correspond to regions between the targets of the probes of the high density array. The short RNA fragments are then separated from the long fragments (e.g., by electrophoresis), labeled if necessary as described above, and then are ready for hybridization with the high density probe array.

In a third approach, sample complexity reduction involves the selective removal of particular (preselected) mRNA messages. In particular, highly expressed mRNA messages that are not specifically probed by the probes in the high density array are preferably removed. This approach involves hybridizing the polyA$^+$ mRNA with an oligonucleotide probe that specifically hybridizes to the preselected message close to the 3' (poly A) end. The probe may be selected to provide high specificity and low cross reactivity. Treatment of the hybridized message/probe complex with RNase H digests the double stranded region effectively removing the polyA$^+$ tail from the rest of the message. The sample is then treated with methods that specifically retain or amplify polyA+ RNA (e.g., an oligo dT column or (dT)n magnetic beads). Such methods will not retain or amplify the selected message(s) as they are no longer associated with a polyA+ tail. These highly expressed messages are effectively removed from the sample providing a sample that has reduced background mRNA.

The oligonucleotide arrays of the present invention may be used to simultaneously monitor the expression of many genes. In certain embodiments, the invention provides for simultaneously monitoring at least about 10, at least about 100, at least about 1000, at least about 5000, at least about 10,000, or at least about 50,000 genes at the same time.

Methods can be used to detect disease, identify differential gene expression between two samples, screening for compounds that upregulate or downregulate gene expression, and so on. For example, where the effects of a drug on gene expression is to be determined the drug will be administered to an organism, a tissue sample, or a cell. Nucleic acids from the tissue sample, cell, or a biological sample from the organism and from an untreated organism tissue sample or cell are isolated, hybridized to an oligonucleotide array of the present invention containing one or more probe directed to the gene of interest and the expression levels of that gene are determined.

Similarly, where the expression levels of a disease marker (e.g., p53, HIV, or HER2) are to be detected (e.g., for the diagnosis of a pathological condition in a patient), comparison of the expression levels of the disease marker in the sample to disease markers from a healthy organism will reveal any deviations in the expression levels of the marker in the test sample as compared to the healthy sample. Correlation of such deviations with a pathological condition provides a diagnostic assay for that condition.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those skilled in the art should, in light of the present disclosure, appreciate that many changes can be made in the specific embodiments that are disclosed and still obtain like or similar results without departing from the spirit and scope of the invention.

Example 1

In this example, a hybridization signal ratio for each probe was obtained by experiments wherein the input amount of target nucleic acid was changed. The hybridization signal ratio of each probe was compared to the concentration ratio. The probe with the ratio closest to the concentration ratio was chosen to represent the gene in a DNA microarray.

Labeled target was hybridized at 2.5 or 1.0 micrograms per 60 microliters with DNA oligonucleotide probes attached to a DNA microarray. The target-probe hybridization events were detected and scanned using fluorescent detection techniques. Each hybridization was performed in triplicate for each target concentration and these results were averaged. The average hybridization signals for each probe were then used to calculate a ratio. This ratio compared one target concentration to a different target concentration for the same probe. Next, the average hybridization signal ratio for the probes on the array was compared with the concentration ratio (2.5:1). The probe having an average hybridization signal that was closest to the concentration ratio was then chosen to represent that gene. See Table 1.

TABLE 1

| Probe | Ratio 2.5/1.0 | Use probe |
|---|---|---|
| Heart cRNA | | |
| IN082:2743U30 | 1.4 | No |
| IN082:3443U30 | 3.4 | Yes |
| IN117:1395U30 | 3.4 | Yes |
| IN117:1604U30 | 7.2 | No |
| Concentration Ratio | 2.5 | |
| Placenta cRNA | | |
| IN082:2743U30 | 1.2 | No |
| IN082:3443U30 | 2.8 | Yes |
| IN117:1395U30 | 3.1 | Yes |
| IN117:1604U30 | 7.2 | No |
| Concentration Ratio | 2.5 | |

Example 2

This example describes an alternative embodiment to that described in Example 1. A set of probes to a given gene was used. The probes were hybridized to compositions derived from liver, then derived from brain, and then derived from heart. A hybridization signal was obtained for each probe hybridized with each composition. Two different hybridization ratios were calculated (liver:heart; liver:brain). The results are indicated in Table 2. The probe having a hybridization ratio profile closest to that of the average of all the probes was chosen to represent that gene and is indicated in bold.

TABLE 2

| Probe | Liver Mean | Heart Mean | Brain Mean | Raw Ratios L/H | L/B | Gene name |
|---|---|---|---|---|---|---|
| AF106860:1134U30 | 1,008,642 | 3,454,074 | 3,017,411 | 0.29 | 0.33 | |
| AF106860:1134U30_1 | 1,248,545 | 4,553,724 | 3,800,282 | 0.27 | 0.33 | |
| AF106860:167U30 | 2,435,602 | 5,287,957 | 5,104,676 | 0.46 | 0.48 | glyceraldehyde-3-phosphate dehydrogenase |
| AF106860:22U30 | 4,565,760 | 6,779,802 | 6,602,698 | 0.67 | 0.69 | |
| AF106860:275U30 | 3,452,296 | 9,503,745 | 9,416,056 | 0.36 | 0.37 | |
| AF106860:870U30 | 4,286,036 | 5,378,198 | 5,078,127 | 0.80 | 0.84 | |
| AF106860:961U30 | 3,323,235 | 5,438,888 | 5,632,372 | 0.61 | 0.59 | |
| average | | | | 0.50 | 0.52 | |
| D10026_1060U30 | 1,420,578 | 259,687 | 120,553 | 5.47 | 11.78 | |
| D10026_507U30 | 9,104 | 1,716 | 3,105 | 5.30 | 2.93 | glutathione-S-transferase |
| D10026_711U30 | 545,335 | 21,219 | 18,714 | 25.70 | 29.14 | theta 1 |

TABLE 2-continued

| Probe | Liver Mean | Heart Mean | Brain Mean | Raw Ratios L/H | L/B | Gene name |
|---|---|---|---|---|---|---|
| D10026_782U30 | 1,336,504 | 434,480 | 632,728 | 3.08 | 2.11 | |
| average | | | | 9.89 | 11.49 | |
| D50580:1629U30 | 81,375 | 5,829 | 8,816 | 13.96 | 9.23 | |
| D50580:1797U30 | 246,600 | 15,072 | 10,796 | 16.36 | 22.84 | carboxyl-esterase 2 |
| D50580:1897U30 | 32,602 | 5,711 | 6,659 | 5.71 | 4.90 | |
| D50580:1956U30 | 359,815 | 161,170 | 162,973 | 2.23 | 2.21 | |
| average | | | | 9.57 | 9.79 | |
| D63673:2351U30 | 23,690 | 6,468 | 28,126 | 3.66 | 0.84 | |
| D63673:2670U30 | 32,099 | 5,234 | 24,798 | 6.13 | 1.29 | peroxisome assembly |
| D63673:2670U30_1 | 20,547 | 3,437 | 15,314 | 5.98 | 1.34 | factor-2 |
| D63673:2756U30 | 113,280 | 7,991 | 64,228 | 14.18 | 1.76 | |
| average | | | | 7.49 | 1.31 | |
| D85189:4050U30 | 1,108,380 | 310,079 | 818,888 | 3.57 | 1.35 | |
| D85189:4097U30 | 1,580,821 | 12,324 | 475,792 | 128.27 | 3.32 | acyl-CoA-synthetase |
| D85189:4174U30 | 969,983 | 9,903 | 329,789 | 97.95 | 2.94 | |
| D85189:4669U30 | 4,442,463 | 78,417 | 2,290,636 | 56.65 | 1.94 | |
| average | | | | 71.61 | 2.39 | |
| J00719_1173U30 | 424,042 | 2,668 | 3,741 | 158.95 | 113.34 | cytochrome P450, subfamily |
| J00719_1320U30 | 1,374,974 | 81,118 | 96,711 | 16.95 | 14.22 | IIB |
| J00719_900U30 | 124,915 | 3,941 | 3,967 | 31.70 | 31.49 | |
| J00719_932U30 | 684,816 | 9,111 | 9,716 | 75.16 | 70.49 | |
| average | | | | 70.69 | 57.38 | |

Example 3

This example describes an embodiment similar to that described in Example 2. However, in this embodiment, three hybridization ratios are determined and used to select the optimal probe to represent the gene of interest. A set of five probes will be used. The probes will be hybridized to compositions derived from three different tissues. As an example, the compositions will be derived from brain, derived from placenta, and derived from heart. A hybridization signal will be obtained for each probe hybridized with each composition. Three different hybridization ratios will then be calculated (brain:placenta; brain:heart; and heart:placenta). The probe having a hybridization ratio profile closest to that of the average of all the probes will be chosen to represent that gene.

The following Table (Table 3) illustrates prophetic results from such a procedure.

TABLE 3

| Probe | Brain:Placenta | Brain:Heart | Heart:Placenta |
|---|---|---|---|
| 1 | 5 | 2 | 2 |
| 2 | 10 | 2 | 5 |
| 3 | 7 | 2 | 3 |
| 4 | 12 | 1 | 10 |
| 5 | 8 | 3 | 4 |
| Average | 8 | 2 | 5 |

In this case, probe 5 would be chosen to represent the gene because its ratio profile (8:3:4) is closest to that of the average ratio profile of all the probes (8:2:5).

Those skilled in the art, having the benefit of the teachings of the present invention as set forth above, can effect numerous modifications thereto. These modifications are to be construed as being encompassed within the scope of the present invention as set forth in the appended claims.

What is claimed is:

1. A method of making an oligonucleotide array, comprising the steps of:
    a) hybridizing three or more candidate probes comprising a nucleic acid sequence with a first composition comprising the target nucleic acid sequence;
    b) determining a first hybridization signal for each candidate probe;
    c) hybridizing the three or more candidate probes with a second and different composition comprising the target nucleic acid sequence;
    d) determining a second hybridization signal for each candidate probe;
    e) calculating a hybridization signal ratio of the first hybridization signal to the second hybridization signal for each candidate probe;
    f) calculating an average hybridization signal ratio for the three or more candidate probes;
    g) selecting the candidate probe by comparing the candidate probe's hybridization signal ratio to the average hybridization signal ratio and choosing the candidate probe having a hybridization signal ratio closest to the average hybridization signal ratio as a first probe; and
    h) constructing an oligonucleotide array comprising a probe comprising the nucleic acid sequence of the first probe.

2. The method of claim 1, wherein steps a) through g) are repeated with a second target sequence and second candidate probes to yield a second probe and constructing a nucleic acid array comprising the first probe and the second probe.

* * * * *